United States Patent [19]

Arya et al.

[11] 4,055,647
[45] Oct. 25, 1977

[54] CONDENSED PYRROLE MERCAPTO COMPOUNDS HAVING HYPOTENSIVE AND DECONGESTANT PROPERTIES

[75] Inventors: Vishwa Prakash Arya; Kuppuswamy Nagarajan, both of Bombay, India

[73] Assignee: Ciba-Geigy Corporation, Ardsley, N.Y.

[21] Appl. No.: 642,503

[22] Filed: Dec. 19, 1975

Related U.S. Application Data

[62] Division of Ser. No. 478,197, June 11, 1974, Pat. No. 3,954,757.

[30] Foreign Application Priority Data

June 14, 1973    Switzerland ................ 8609/73

[51] Int. Cl.$^2$ ........................................ A61K 31/505
[52] U.S. Cl. .................................. 424/251; 424/263; 424/273 R; 424/274
[58] Field of Search ............... 424/251, 263, 273, 274

[56]     References Cited
U.S. PATENT DOCUMENTS

| 3,377,247 | 4/1968 | Ebce ................................ 424/273 |
| 3,586,695 | 6/1971 | Wysong et al. .................. 260/309.6 |
| 3,954,757 | 5/1976 | Arya et al. .................... 260/256.5 R |

OTHER PUBLICATIONS

Wilson & Griswold–"Textbook of Organic Medical & Pharmaceutical Chemistry", 4th ed., 1962, pp. 390–391.

*Primary Examiner*—Leonard Schenkman
*Attorney, Agent, or Firm*—John J. Maitner

[57]            ABSTRACT

The present invention relates to condensed pyrrole mercapto compounds, especially to optionally substituted indole or aza-indole mercapto derivatives, which compounds have ophthalmological and hypotensive properties, in particular vasoconstrictor, especially decongestant properties. It further relates to pharmaceutical compositions containing these compounds. An illustrative example is 3-(2-imidazolin-2-ylthio)-indole hydrochloride or hydroiodide.

3 Claims, No Drawings

CONDENSED PYRROLE MERCAPTO COMPOUNDS HAVING HYPOTENSIVE AND DECONGESTANT PROPERTIES

This is a division, of application Ser. No. 478,197, filed June 11, 1974 now U.S. Pat. No. 3,954,757.

The subject of this invention is the preparation of a compound of the formula I

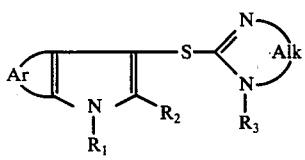

where Ar is a grouping which along with the adjacent carbon atoms form an o-arylene or an o-heteroarylene residue, each of $R_1$ and $R_3$ independently is hydrogen or a radical of aliphatic character, $R_2$ is a hydrogen atom, a radical of aliphatic character or a free carboxyl group or functional derivative thereof and Alk represents a substituted or unsubstituted alkylene or alkenylene radical contributing 2–5 carbon atoms to the ring, their tautomers and salts.

The residue Ar forms together with the two adjacent carbon atoms of the pyrrol ring a carbocyclic or monoheterocyclic radical of aromatic character. A carbocyclic radical of aromatic character is especially an o-phenylene radical which may be substituted by one, two or more identical or different substituents attached to any one of the positions available for substitution. A monoheterocyclic residue of aromatic character is primarily a monoaza, monooxa- or monothiacyclic group of aromatic character which, in accordance to the o-phenylene residue, may be substituted. A monoazacyclic residue of aromatic character is e.g. an o-pyridylene, while monooxacyclic and monothiacyclic residues of aromatic character are o-furylene and o-thienylene groups, respectively.

Substituents of the carbocyclic and monoheterocyclic radicals of aromatic character are optionally substituted hydrocarbon radicals, e.g. optionally substituted aliphatic, cycloaliphatic, cycloaliphatic-aliphatic, aromatic or araliphatic hydrocarbon radicals, with aliphatic or cycloaliphatic radicals preferably being saturated. In cycloaliphatic hydrocarbon radicals the cyclic moiety is preferably monocyclic, but it can also be bicyclic or polycyclic.

An aliphatic hydrocarbon radical which can optionally be substituted is in particular an alkyl, alkenyl or alkinyl radical, in particular a straight-chain or branched lower alkyl, lower alkenyl or lower alkinyl radical. Examples of substituents of aliphatic hydrocarbons are free, esterified or etherified hydroxy groups, such as lower alkoxy, lower alkenyloxy groups or halogen atoms or functional derivatives of a carboxy group, e.g. lower alkoxycarbonyl groups.

The term "lower" as used hereinbefore or hereinbelow in connection with the definition of organic compounds, groups and radicals, signifies that such compounds, groups and radicals contain preferably up to and including 7 carbon atoms.

Examples of lower alkyl groups are preferably methyl, ethyl, n-propyl, isopropyl, n-butyl, isobutyl, sec. butyl, tert. butyl, n-pentyl, isopentyl, neopentyl, n-hexyl, iso-hexyl or n-heptyl groups. Lower alkenyl is e.g. the allyl or 2-methylallyl group and lower alkinyl groups are preferably propargyl groups. Substituted lower alkyl groups are e.g. the trifluoromethyl group or an optionally esterified carboxymethyl group, e.g. the alkoxycarbonylmethyl group.

Further substituents of the carbocyclic or monoheterocyclic radicals of aromatic character are free, etherified or esterified hydroxy and etherified mercapto groups, e.g. alkoxy groups and halogen atoms, in particular the methoxy, ethoxy, n-propoxy, isopropoxy, n-butyloxy, isobutyloxy, tert. butyloxy, sec. butyloxy groups and alkylmercapto groups, e.g. methylmercapto or ethylmercapto groups. Also possible are the lower alkoxy groups with 2 to 3 carbon atoms in the alkoxy moiety which are substituted by a free, etherified or esterified hydroxyl group, e.g. as hydroxy-lower alkoxy radical the 2-hydroxyethoxy radical, as lower alkoxy-alkoxy radical the 2-methoxyethoxy radical, and as halo-lower alkoxy radical the 2-chloroethoxy radical, and as optionally substituted aryl-lower alkoxy radical, for example a phenyl-lower alkoxy radical, in particular the benzyloxy radical, ans as optionally substituted aryloxy radical the phenyloxy radical.

Halogen atoms are primarily fluorine, chlorine or bromine atoms, but can also be iodine atoms.

The aromatic radicals mentioned in the last cited groups can in their turn be substituted by the substituents and functional groups defined hereinbefore as in the enumeration of the individual hydrocarbon group. The aromatic radicals of the substituents can also be substituted by an acyloxy group, for example by a lower alkanoyloxy group, in particular by the acetyloxy or propionyloxy group.

As further substituents of the carbocyclic and monoheterocyclic radicals of aromatic character are to be mentioned the nitro group, the free or substituted amino group, e.g. a lower alkylamino group, in particular the methylamino or ethylamino group or an acylamino group, e.g. a lower alkanoylamino group, in particular the acetylamino or the propionylamino group. As disubstituted amino group there may be mentioned the N,N-di-lower alkylamino group, e.g. the N,N-dimethylamino or the N,N-diethylamino groups.

Examples of further secondary and tertiary amino groups are: N-ethyl-N-methylamino, n-propylamino, di-n-propylamino, isopropylamino, diisopropylamino or di-n-butylamino groups.

Further substituents of the carboaromatic or heteroaromatic radicals are acyl groups, free or functionally modified carboxy groups, in particular esterified carboxy groups, e.g. the methoxycarbonyl or ethoxycarbonyl groups or lower alkanoyl groups, for example the acetyl or the propionyl groups.

Radicals of aliphatic character of the substituents $R_1$, $R_2$ and $R_3$ are optionally substituted hydrocarbon radicals, e.g. aliphatic, cycloaliphatic, cycloaliphtic-aliphatic, aromatic or araliphatic hydrocarbon radicals.

An aliphatic hydrocarbon radical preferably has a maximum of 7 carbon atoms and is e.g. lower alkyl, lower alkenyl or lower alkinyl. A lower alkyl radical is especially one mentioned above. A lower alkenyl group preferably is allyl or methallyl, and a lower alkinyl group propargyl. A cycloaliphatic hydrocarbon residue preferably has 3–8 ring carbon atoms, and represents, for example, a cycloalkyl, e.g. cyclopentyl or cyclohexyl group. A cycloaliphatic-aliphatic hydrocarbon radical preferably contains as a cycloaliphatic residue one of those mentioned above and represents preferably a cycloalkyl-lower alkyl radical, e.g. cyclopentylmethyl, cyclohexylmethyl, or cyclohexylethyl. The above mentioned hydrocarbon radicals may be mono-, di or poly-substituted aliphatic hydrocarbon radicals.

Aliphatic hydrocarbon radicals can be substituted by a free hydroxy, etherified or esterified hydroxy group, free or substituted amino group or nitro group, a lower alkylenedioxy group or by substituents which have already been defined hereinbefore.

Cycloaliphatic hydrocarbon radicals can be substituted by lower alkyl radicals, in particular by the lower alkyl radicals which have already been defined hereinbefore in detail or by the substituents which have already been mentioned in the enumeration of the aliphatic hydrocarbon radicals.

The aliphatic radical of a cycloaliphatic-aliphatic or araliphatic group can be substituted principally by one of the lower alkyl radicals already defined hereinbefore. The aromatic portion of the araliphatic group may be substituted for example by substituents mentioned above for an o-phenylene radical.

Aliphatic hydrocarbon radicals of the substituents $R_1$, $R_2$ and $R_3$ are in particular alkyl radicals, particularly however, lower alkyl radicals.

The bivalent alkylene and alkenylene radical "Alk" can be monosubstituted or polysubstituted, in particular by free or substituted hydroxy or mercapto groups such as etherified hydroxy or mercapto groups, e.g. lower alkoxy groups, in particular methoxy and ethoxy groups, or e.g. by lower alkylmercapto groups, in particular methylmercapto or ethylmercapto groups. Also possible are esterified hydroxy groups, e.g. lower alkanoyloxy groups, in particular the acetyloxy group, halogen atoms, especially fluorine, chlorine or bromine atoms, the oxo group or functionally modified oxo groups, e.g. the hydroxyimino, hydrazone or semicarbazone radical. A lower alkylene or alkenylene radical "Alk" can be, for example, the 1,2-ethylene, 1,2- or 1,3-propylene, 2,3-, 2,4- or 1,5-pentylene, vinylene or 1,3-propenylene radical. Besides representing an alkyl group, the substituent $R_2$ represents above all a carboxy group, but it can also represent a functional derivative of a carboxy group, e.g. a lower alkoxycarbonyl group, in particular the methoxycarbonyl, n-propoxycarbonyl or n-butoxycarbonyl group. Also possible are nitrogen-containing functional derivatives of the carboxy group, e.g. the carbamoyl group, which can be optionally substituted at the nitrogen atom, for example a carbamoyl group which is substituted by N-lower alkyl, in particular the N-methylcarbamoyl, N,N-dimethylcarbamoyl, N-ethylcarbamoyl or the N,N-diethylcarbamoyl groups. As further nitrogen-containing functional derivatives of the carboxy group mention may also be made of the nitriles.

The new compounds exhibit valuable pharmacological properties. In addition to ophthalmological and hypotensive effects, they primarily show vasoconstrictor, especially decongestant, e.g. nasal decongestant properties. The new compounds are, therefore, useful as pharmacologically effective compounds, and may be used as nasal decongestant agents in the treatment of colds for which purpose daily doses of about 0.1 to 50 mg may be used. As anti-hypertensive agents they are useful at a daily dose of 50–500 mg. They are also useful as intermediate products in the preparation of other valuable compounds, especially of pharmacologically active substances.

The invention concerns primarily compounds of the formula (Ia)

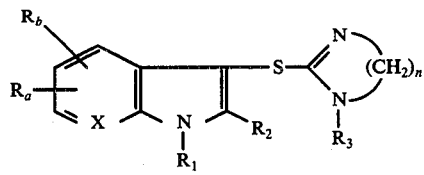

Ia wherein X is nitrogen or represents the group CH, and each of Ra und Rb is hydrogen or any of the substituents of the carbocyclic or heterocyclic aromatic radicals mentioned earlier, each of $R_1$ and $R_3$ independently is hydrogen or a lower alkyl group, $R_2$ is hydrogen, lower alkyl or a free or esterified carboxy group as for example an alkoxy carbonyl group and n is an integer denoting 2–5, their tautomers and acid addition salts.

Of special interest in this invention are compounds of formula Ia in which X represents the group CH, each of $R_1$ and $R_3$ independently is hydrogen or lower alkyl and $R_2$ is hydrogen, lower alkyl, a free carboxy or methoxycarbonyl or ethoxycarbonyl group, and each of $R_a$ and $R_b$ is hydrogen, lower alkyl, halogen or a lower alkoxy group and n is an integer denoting 2–4, their tautomers and acid addition salts.

Expecially the invention concerns compounds of formula Ia in which X represents the group CH, $R_1$ and $R_3$ independently is hydrogen or lower alkyl and $R_2$ is hydrogen, lower alkyl or a free carboxy group, and each of $R_a$ and $R_b$ is hydrogen, halogen or a lower alkoxy group and n is an integer denoting 2–4, their tautomers and acid addition salts.

Furthermore the invention concerns in particular compounds of formula Ia in which X represents the group CH, $R_1$ and $R_3$ are hydrogen or methyl and $R_2$ is hydrogen, methyl or a free carboxy group, and each of $R_a$ and $R_b$ is hydrogen, chlorine, bromine or methoxy, and n is an integer denoting 2–4, their tautomers and acid addition salts.

Of the new compounds of formula Ia is especially named the 3-(2-imidazolin-2-ylthio)-indole hydrochloride and hydoiodide.

The new compounds of the general formula I are obtained by methods which are in themselves known, as for example a. by reacting a compound of the formula II wherein $R_3$ and "Alk" have the meanings defined in formula I

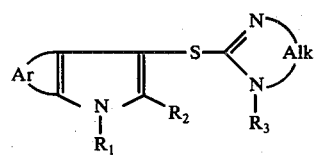

I or a tautomer thereof with a compound of the formula III

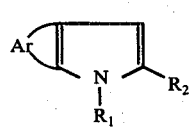

III wherein R₁ and R₂ have the meanings given under formula I, in the presence of a suitable oxidising agent and if desired converting the resulting compound to an acid addition salt thereof.

This process is performed with compounds of the formula II and III in the presence of an oxidising agent, especially halogen, particularly, iodine or bromine in the presence of suitable solvents and other additives such as an alkali metal salt of a hydrohalic acid especially potassium salt of hydroiodic or hydrochloric acid. Other oxidising agents may also be used such as ferric chloride or ferricyanide salts, advantageously, in the presence of a suitable solvent.

b. In a second process a compound of the formula IV

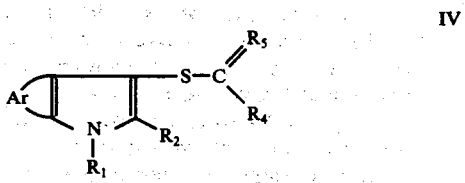

(IV)

wherein R₁, R₂ and Ar have the meanings given under I, R₄ is a free or functionally converted derivative of a hydroxy group, a free mercapto group or a modified mercapto group or amino group, R₅ is an oxygen or sulphur atom, or an imino group or R₄ amd R₅ taken together represents a triple bonded nitrogen atom (nitrilo residue) is reacted with a compound of the general formula V,

(V)

in which R₆ and R₇ each depending on the meaning of R₄ and R₅ represents an amino, imino, hydroxy or functionally converted hydroxy, whereby the substituents R₄ – R₇ contain at least 2 nitrogen atoms in order to obtain the ring of formula VI

(VI)

and if desired, converting a resulting compound to an acid addition salt therof.

The above defined reaction results with compounds of formula IV, which, depending on the meaning of the substituents R₄ and R₅ are primarily derivatives of the thiocarbonic, dithiocarbonic or trithiocarbonic acid, such as amides, imides, nitriles, halides or intramolecular anhydrides.

The substituents R₆ and R₇ of the general formula V are amino, imino, hydroxy or a reactive esterified hydroxy group.

For example in compounds of the general formula IV the substituent R₄ is an NHR₃ group and R₅ an unsubstituted amino group and in compounds of formula V each of the substituent R₆ and R₇ is a hydroxy, especially, a reactive esterified hydroxy group, particularly a halogen atom.

As a further example, in a compound of formula IV the substituent R₄ is an NHR₃ group and R₅ an oxo or a thioxo group and R₆ in the compound of formula V a hydroxy or reactive esterified hydroxy group as mentioned before and R₇ an amino group. Furthermore in a compound of formula IV R₄ is a hydroxy, mercapto or a reactive esterified hydroxy group and R₅ an imino group and in the compound of formula V the substituent R₆ is an NHR₃ group and R₇ a hydroxy or a reactive esterified hydroxy group as described before.

In a further example, the substituent R₄ of compound of formula IV is a hydroxy, reactive esterified hydroxy or mercapto group and R₅ an oxo, thioxo group or R₄ and R₅ taken together in the residue

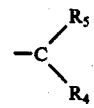

as a nitrilo residue form a nitrile and in the compound V R₆ is an NHR₃ group and R₇ an amino group.

Preferably in the above process as a compound of formula IV a pseudothiourea is used in which the substituent R₄ is an NHR₃ group and R₅ an amino group and as compound of formula V a reactive diester in which R₆ and R₇ each represent a hydroxy group is used.

The reaction of a pseudothiourea compound of formula IV with a reactive diester of an alkanediol of formula V is carried out by using a diester with an above defined strong acid, in particular with a hydrohalic acid. The reaction is carried out in a suitable solvent, in particular a lower alcohol e.g. ethanol and, if desired, in the presence of an acid-binding medium, e.g. an alkalimetal or alkaline earth metal hydroxide, carbonate or hydrogen carbonate.

c. According to a third process compounds of formula I may be prepared by reacting a compound of the general formula VII

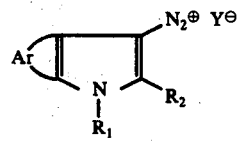

VII in which R₁, R₂ and Ar have the meanings defined under formula I and Y is an anion of an inorganic acid with a compound of the general formula II

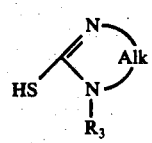

II wherein R₃ has the same meaning as defined under formula I. The reaction is carried out by reacting a diazonium salt of formula VII, in which Y⁻ is an anion of an inorganic acid, for example hydrochloric acid, sulphuric acid, fluoboric acid or phosphoric acid with a compound of formula II, wherein R₃ has the above defined meaning.

When a compound of formula II is added to a diazonium salt solution of formula VII in an acidic or neutral solution, an isothiouronium salt is formed which is substituted at the sulphur atom.

Resulting compounds may be converted into others of the formula I, for example, by modifying, introducing or splitting off substituents according to methods known per se. Substituents attached to aromatic rings may be converted to other substituents, for example, nitro groups into amino groups by reduction in the usual manner, for example by treatment with catalytically activated hydrogen.

The reactions of this invention are carried out in the usual manner, at room temperature or with cooling or heating, under atmospheric or superatmospheric pressure, if necessary, in the presence or absence of diluents, catalysts and condensing agents, and/or in the atmosphere of an inert gas, e.g. nitrogen.

The invention further includes any new compound formed as an intermediate product.

The starting materials to be used in the present process are advantageously those which give rise to the compounds referred to above as being especially valuable.

The starting materials are known or, in so far as they are new, they can be prepared by known methods. Thus, compounds of the formula II are prepared by reacting an alkylenediamine of the formula $R_3NH-Alk-NH_2$ with carbon disulphide or with thiophosgene. Compounds of the formula III are well-known in literature and may be prepared apart from other methods by the Fischer indole cyclization of suitable hydrazone compounds.

Starting materials of the formula IV are prepared for example by reacting an optionally substituted thiourea with compounds of the formula III in the presence of a suitable oxidising agent as described under the first process for the preparation of pseudo thiourea compounds. Other starting materials of the formula IV may be obtained by reacting a suitable thiocyanate, thiocarbonic acid or one of its derivatives with compounds of the formula III.

Compounds of the formula VII of the third process can be prepared by the conventional diazotization of 3-amino derivative of the formula III in the presence of a nitrite such as an alkali nitrite, for example sodium nitrite or an organic nitrite for example amyl nitrite in the presence of a suitable acid such as an inorganic acid, for example hydrochloric, sulphuric, phosphoric or fluoboric acids. The diazonium salts are usually prepared and reacted in solution.

Depending on the reaction conditions employed, the new compounds are obtained in the free form or in the form of their salts. The latter are acid addition salts such, for example, as pharmaceutically acceptable, non-toxic acid addition salts, for example, salts with inorganic acid such as hydrochloric, hydrobromic, nitric, sulphuric or phosphoric acids, or with organic acids such as organic carboxylic acids, for example, acetic, propionic, glycollic, malonic, succinic, maleic, hydroxymaleic, furmaric, malic, tartaric, citric, benzoic, cinnamic, mandelic, salicylic, 4-aminosalicylic, 2-phenoxybenzoic, 2-acetoxy-benzoic, embonic, glucuronic, nicotinic or isonicotinic acid, or with organic sulphonic acids, for example, methanesulphonic, ethanesulphonic, 2-hydroxyethanesulphonic, 1,2-ethanedisulphonic, benzenesulphonic, paratoluenesulphonic or 2-naphthalenesulphonic acid. These and other acid addition salts may also be used as intermediate products, for example, for purifying the free compounds or in the manufacture of other salts, as well as for identification purposes. Salts particularly suitable for the last mentioned purpose are, for example, those with acid organic nitro compounds, for example, picric, picrolonic or flavianic acid, or with metallic complex acids, for example, phosphotungstic, phosphomolybdic, chloroplatinic acid or Reinecke acid, either mono-salts or poly-salts may be formed.

Free compounds may be converted into their acid addition salts, for example, by treatment with acids, such as the acids mentioned above, for instance by treating a solution of the base in a suitable inert solvent or solvent mixture with an acid or a solution thereof, or with a suitable ion exchange resin. Salts may also be obtained in the form of their hydrates, or they may contain solvent of crystallization.

A resulting salt may be converted into the free compound, for example, by treatment with a base, such as an alkali or alkaline earth metal hydroxide or carbonate, or with ammonia or with a suitable ion exchange resin.

A resulting salt may also be converted into another salt, for example, by treatment with an ion exchange resin or by reacting a salt with an inorganic acid with a metal salt, for example, a sodium, barium or silver salt, of an acid in a suitable solvent in which the resulting inorganic compound is insoluble.

In view of the close relationship between the new compounds in the free and in the form of their salts, whenever a free compound or a salt is referred to in this context, the corresponding salt and free compound, respectively, is also intended, provided such is possible or appropriate under the circumstances.

Mixtures of isomers may be resolved into their constituents by known methods. Thus, for example, resulting racemates may be resolved into the optically active d-forms and l-forms by crystallization from optically active solvents, or by treating the racemic compounds with an optically active form of an acid, containing an asymmetric carbon atom, preferably in the presence of a suitable solvent. Particularly suitable optically active forms of acids are d-tartaric acid and l-tartaric acid, as well as the optically active forms of maleic, mandelic, camphor-10-sulphonic or quinic acid. Resulting salts may be converted into other salts or into the free and optically active bases, and an optically active base may be converted into an acid addition salt by the methods referred to above.

The invention includes also any modification of the present process in which an intermediate obtained at any stage of the process is used as starting material and any remaining step or steps is or are carried out, or in which the process is discontinued at any stage thereof, or in which a starting material is formed under the reaction conditions or used in the form of a derivative, for example, a salt thereof.

The invention also includes pharmaceutical preparations which contain one of the new compounds or a salt thereof in admixture with a pharmaceutical organic or inorganic solid or liquid carrier suitable for enteral, as for example oral, parenteral or topical administration.

Suitable dosage units are dragees, tablets, capsuls, suppositories or ampoules. These pharmaceutical preparations contain per dosage unit, e.g. 0.01–100 mg, preferably 0.1–50 mg of the new compound or a pharmaceutically acceptable acid addition salt thereof. It is moreover possible to use corresponding amounts of preparations, solutions, suspensions and emulsions which are not administered as individual doses, such as in the case of drops, syrups and elixirs.

In dosage units for oral administration, the content of active substance is preferably between 10% and 90%. Such dosage units are produced by the combination of the active substance with, e.g. solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium or calcium stearate, or polyethylene glycols, to form tablets or dragee cores.

The latter are coated, for example, with concentrated sugar solutions which may also contain, e.g. gum arabic, talcum and/or titanium dioxide; or with a lacquer dissolved in readily volatile organic solvents or solvent mixtures. Dyestuffs can be added to these coatings; e.g., for identification of the various doses of active substance. Further suitable oral dosage units are hard gelative capsules, as well as soft closed capsules made from gelatine and a softener such as glycerin. The hard capsules contain the active substance preferably as a granulate in admixture with lubricants such as talcum or magnesium, and, optionally, stabilisers such as sodium metabisulphite ($Na_2S_2O_2$) or ascorbic acid. In soft capsules the active substance is preferably dissolved or suspended in suitable liquids such as liquid polyethylene glycols, to which likewise stabilisers may be added.

Suitable dosage units for rectal administration are, e.g. suppositories consisting of a combination of an active substance with a suppository mixture based on natural or synthetic triglycerides (e.g. cocoa butter), polyethylene glycols or suitable higher fatty alcohols; and gelatine rectal capsules containing a combination of the active substance with polyethylene glycols.

Ampoule solutions for parenteral administration, particularly intramuscular or intravenous administration, contain, for example, a compound of the general formula I, in a concentration of preferably 0.5 – 5%, as an aqueous dispersion prepared with the aid of conventional solubility-promoting agents and/or emulsifiers; or preferably an aqueous solution of a pharmaceutically acceptable, water-soluble acid addition salt of a compound of the general formula I.

In the case of liquids to be taken orally, such as syrups and elixirs, the concentration of the active substance is designed to enable single doses to be easily measured out, e.g. as the content of a tea-spoon or of a measuring spoon containing, e.g. 5 ml , or as a multiple of this volume. Suitable syrups are, for example, solutions of water-soluble acid addition salts, or suspensions of insoluble but absorbable acid addition salts, in aqueous solutions of sugars and/or alkanepolyols, such as unrefined sugar or sorbitol or glycerin, flavourings and aromatics, as well as, optionally, preservatives and stabilisers. Elixirs are aqueous-alcoholic solutions of a compound of the general formula I, or of pharmaceutically acceptable salts thereof, which may likewise contain the additives mentioned in the case of syrups. Further oral preparations to be mentioned are dropping-solutions which usually have a higher alcohol content and, at the same time, a higher content of active substance, so that a single dose can be measured out, e.g. as 10 to 50 drops. Furthermore compounds of formula I, especially its pharmaceutically acceptable salts can be used therapeutically in the form of drops in a solution.

The following Examples a) to g) illustrate the production of some typical preparations, but these examples, however, in no way represent the only embodiments of such preparations.

a. An amount of 250.0 g of active substance is mixed with 550.0 g of lactose and 292.0 g of potato starch; the mixture is moistened with an alcoholic solution of 8 g of gelatine, and granulated through a sieve. The obtained granulate is dried and 60.0 g of potato starch, 60.0 g of talcum, 10.0 g of magnesium stearate and 20.0 g of colloidal silicon dioxide are mixed in; the mixture is then pressed into 10,000 tablets each weighing 125 mg and each containing 25 mg of active substance. The tablets can optionally be provided with grooves for a more precise adjustment of the dosage amount.

b. A granulate is prepared from 100.0 g of active substance, 379.0 g of lactose, and the alcoholic solution of 6.0 g of gelatine; the granulate is then dried and mixed with 10.0 g of colloidal silicon dioxide, 40.0 g of talcum, 60.0 g of potato starch and 5.0 g of magnesium stearate; and the mixture finally pressed to obtain 10,000 dragee cores. These are subsequently coated with a concentrated syrup made from 533.5 g of crystallised saccharose, 20.0 of shellac, 75.0 g of gum arabic, 250.0 g of talcum, 20.0 g of colloidal silicon dioxide and 1.5 g of dyestuff. After drying, the obtained dragees each weigh 150 mg and each contain 10 mg of active substance.

c. An amount of 20.0 g of active substance is dissolved in 1500 ml of boiled pyrogen-free water, the solution being then made up to 2000 ml with similarly treated water. The solution is filtered off and filled into 1000 ampoules each containing 2 ml, these being finally sterilised. A 2 ml ampoule contains 20 mg or 1.0% of active substance.

d. An amount of 25.0 g of active substance and 1975 g of finely ground suppository foundation substance (e.g. cocoa butter) is thoroughly mixed and then melted. The melt is maintained homogeneous by stirring whilst being poured out to form 1000 suppositories each weighing 2.0 g. They each contain 25 mg of active substance.

e. For the preparation of a syrup containing 0.25% of active substance, 1.5 liters of glycerin, 42 g of p-hydroxybenzoic acid methyl ester, 18 g of p-hydroxybenzoic acid-n-propyl ester and, with slight heating, 25.0 g active substance are dissolved in 3 liters of distilled water; additions are then made to the solution of 4 liters of 70% sorbitol solution, 1000 g of cryst. saccharose, 350 g of glucose and an aromatic, e.g. 250 g of Orange Peel Soluble Fluid of the firm Eli Lilly and Co., Indianapolis, or 5 g natural lemon aroma and "Halb und Halb" essence, both manufactured by the firm Haarmann und Reimer, Holzminden, Germany; the obtained solution is filtered, and the filtrate made up with distilled water to 10 liters.

f. In order to prepare a dropping solution containing 1.5% of active substance, 150.0 g of active substance and 30 g of sodium cyclamate are dissolved in a mixtrue of 4 liters of ethanol (96%) and 1 liter of propylene glycol. A mixture is the prepared separately of 3.5 liters of 70% sorbitol solution with 1 liter of water; this mixture is subsequently added to the above mentioned active substance solution. An addition is thereupon made of an aromatic, e.g. 5 g of cough-sweet aroma or 30 g of grapefruit essence, both from the firm Haarmann and Reimer, Holzminden, Germany; and the whole is afterwards well mixed, filtered, and made up with distilled water to 10 liters.

g. In order to prepare a solution for using therapeutically the form of drops, following compositions are added:

| | |
|---|---|
| active substance (compound of formula I) | 1 g |
| para-hydroxybenzoic acid propylester | 0,8 g |
| para-hydroxybenzoic acid methylester | 0,4 g |
| de-ionized water, to make up | 1000 cc. |

The following examples illustrate the production of the new compounds of the general formula I; these examples, however, are not intended in any way to limit the scope of the invention. The temperatures are expressed in degrees Centigrade.

EXAMPLE 1

A mixture of 11.7 g indole in 100 ml methanol and 10.2 g 2-imidazolidinethione in 150 ml methanol is added to a well-stirred solution of 25.4 g iodine and 50 g potassium iodine in 100 ml water. The mixture is stirred for 2 hours at room temperature. The clear solution is concentrated in vacuo to one third of the original volume and cooled. The solid which separates is filtered off, dried and recrystallised from alcohol-ether to give 3-(2-imidazolin-2-ylthio)-indole hydriodide of the formula

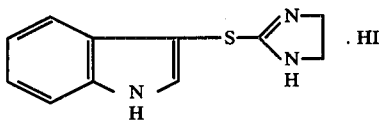

melting at 210°–211°.

By passing a solution of 10 g of above hydriodide in 50 ml methanol through a column of 100 g Amberlite IRA-400 (chloride form) resin in methanol, the hydrochloride is obtained. After recrystallization from alchohol-ether, it melts at 240°–241°.

EXAMPLE 2

A mixture of 11.7 g indole in 50 ml methanol and 11.6 g 1,4,5,6-tetrahydro-2- pyrimidinethiol in 100 ml methanol is added to a well-stirred solution of 25.4 g iodine and 50 g potassium iodide in 100 ml water. The mixture is stirred for 12 hours at room temperature and cooled. The crystalline product is filtered off. The filtrate is concentrated to one third of the original volume, and cooled to yield more of the resulting product. The combined product is recrystallised from alcohol to give 3-(1,4,5,6-tetrahydro-2-pyrimidinylthio)-indole hydriodide, melting at 251°.

By passing a solution of 7 g of above hydriodide in 35 ml methanol through a column of 70 g Amberlite IRA-400 (chloride form) resin in methanol, the hydrochloride is obtained. Upon recrystallization from alcohol-ether, it is obtained as a monohydrate melting at 125°–126°.

EXAMPLE 3

A mixture of 3,2 g indole-2-carboxylic acid in 50 ml methanol and 2 g 2-imidazolidinethione in 100 ml methanol is added to a well-stirred solution of 3 g iodine and 25 g potassium iodide in 50 ml water. After being stirred for 2 hours at room temperature, the mixture is filtered to remove the product. The filtrate is concentrated and cooled to give further yield. The combined product is recrystallised from alcohol-ether to give 3-(2-imidazolin-2-ylthio)-indole-2-carboxylic acid hydriodide melting above 310°.

By passing a solution of 2 g of the above hydriodide in 10 ml methanol through a column of 20 g Amberlite IRA-400 (chloride form) resin in methanol, the hydrochloride is obtained. Upon recrystallization from methanol-ether, it is obtained as a monohydrate melting at 187°–188° (with decomposition).

The free base is obtained by treatment of an aqueous suspension of the hydriodide with sodium bicarbonate. Upon crystallization from aqueous alcohol it melts at 204°–206°.

EXAMPLE 4

A mixture of 6.4 g indole-2-carboxylic acid in 25 ml methanol and 4.6 g 1,4,5,6-tetrahydro-2-pyrimidinethiol in 50 ml methanol is added to a well-stirred solution of 10.1 g iodine and 16.3 g potassium iodide in 50 ml water. The mixture is stirred at room temperature for 1½ hours, and cooled. The crystalline product is filtered off. A second yield is obtained by concentrating the filtrate to a small volume and cooling. The combined product is recrystallised from hot water to give 3-(1,4,5,6-tetrahydro-2-pyrimidinylthio)-indole-2-carboxylic acid hydriodide melting at 252°.

EXAMPLE 5

A mixture of 2.8 g 7-azaindole in 25 ml methanol and 3.5 g 1,4,5,6-tetrahydro-2-pyrimidinethiol in 50 ml methanol is added to a well-stirred solution of 7.6 g iodine and 15 g potassium iodide in 50 ml water. The mixture is stirred at room temperature for 14 hours and filtered. The precipitate is washed with water and ether and then recrystallised from water to give 3-(1,4,5,6-tetrahydro-2-pyrimidinylthio)-7-aza-indole hydriodide melting at 294°–295°.

EXAMPLE 6

A solution of 19.6 g of 5-bromo-indole in 50 ml of methanol is added to a stirred solution of 50 g potassium iodide and 25.4 g of iodine in 150 ml of water at room temperature. The mixture is further treated with a solution of 11.6 g of 1,4,5,6-tetrahydro-2-pyrimidinethiol in 270 ml of warm methanol. The reaction mixture is then stirred at room temperature for 2 hours, filtered and the filtrate is concentrated to one-fifth of the original volume and cooled. A crystalline precipitate is formed. This is filtered and recrystallised from a mixture of methanol, ethylacetate and ether to yield 5-bromo-3-(1,4,5,6-tetrahydro-2-pyrimidinylthio)-indole hydriodide which melts at 241°–242°.

EXAMPLE 7

A solution of 11.7 g of indole in 100 ml of methanol is added portionwise to a stirred solution of 50 g potassium iodide and 25.4 g of iodine in 150 ml of water at room temperature. This mixture is further treated with a solution of 13 g of 1-methyl-1,4,5,6-tetrahydro-2-pyrimidinethiol in 150 ml of methanol. The reaction mixture is then stirred at room temperature for 2 hours, filtered and the filtrate concentrated to one-fourth of the original volume and cooled. A crystalline precipitate is formed. This is filtered and recrystallised from a mixture of methanol, ethyl acetate and ether to yield 3-(1-methyl-1,4,5,6-tetrahydro-2-pyrimidinylthio)-indole hydriodide which melts at 207°.

The starting material is prepared as follows:

To a solution of 162 g 3-methylaminopropylamine in 600 ml of 50% aqueous ethanol, 121 ml carbondisulphide is added dropwise so that the temperature does not exceed 60°. The reaction mixture is heated at 60° for 2 hours and 15 ml concentrated hydrochloric acid is added and then the reaction mixture is heated under reflux for 16 hours at 100°. On cooling to −5°, a crystalline precipitate is formed which is filtered and recrystallised from isopropanol to afford 1-methyl-1,4,5,6-tetrahydro-2-pyrimidinethiol which melts at 125°.

EXAMPLE 8

A solution of 9.36 g of indole in 60 ml methanol is added dropwise to a well-stirred solution of 40 g potassium iodide and 20.3 g of iodine in 120 ml of water at room temperature. This is reacted with a solution of 10.6 g of 2-mercapto-1,4,5,6-tetrahydro-5-pyrimidinol in 1800 ml of 50% aqueous methanol. The reaction mixture is stirred at room temperature for 2 hours and worked up in the manner, described under Example 1 to yield 3-(5-hydroxy-1,4,5,6-tetrahydro-2-pyrimidinylthio)-indole hydriodide which melts at 228°–229° (with decomposition) after recrystallization from a mixture of methanol, ethyl acetate and ether.

The starting material is prepared as follows:

A mixture of 42 g 1,3-diamino-2-propanol and 150 ml of 50% ethanol is treated dropwise with 31 ml carbon disulphide and the reaction mixture heated at 60° for 2 hours, 4 ml of concentrated hydrochloric acid is added and the reaction mixture is heated for 10 hours at 100°. It is cooled to 5° and the crystalline precipitate formed, is filtered off and recrystallized from 50% aqueous ethanol to yield 2-mercapto-1,4,5,6-tetrahydro-5-pyrimidinol which melts at 236°.

EXAMPLE 9

A solution of 28.98 g of indole-2-carboxylic acid in 300 ml of methanol is added to a well-stirred solution of 90 g of potassium iodide and 45.6 g of iodine in 270 ml of water at room temperature. This mixture is further treated with a solution of 23.4 g of 1-methyl-1,4,5,6-tetrahydro-2-pyrimidinethiol in 420 ml of warm methanol. The reaction mixture is stirred for 2 hours at room temperature and worked up in the manner described unter Example 1 to yield 3-(1-methyl-1,4,5,6-tetrahydro-2-pyrimidinylthio)-indole-2-carboxylic acid hydriodide which melts at 230°–231° after recrystallization from a mixture of methanol, ethyl acetate and ether.

EXAMPLE 10

A solution of 5.7 g of 5-methoxy-indole-2-carboxylic acid in 70 ml of hot methanol is added portionwise to a solution of 15 g potassium iodide and 7.6 g of iodine in 45 ml of water. This is further treated with a solution of 3.48 g of 1,4,5,6-tetrahydro-2-pyrimidinethiol in 70 ml of hot methanol, stirred at room temperature for 2 hours and filtered. The filtrate is worked up in the manner described under Example 1 to yield 5-methoxy-3-(1,4,5,6-tetrahydro-2-pyrimidinylthio)-indole-2-carboxylic acid hydriodide which melts at 239°–240° after recrystallization from a mixture of methanol, ethyl acetate and ether.

EXAMPLE 11

A solution of 19.65 g of 2-methylindole in 250 ml of methanol is added to a well-stirred solution of 75 g of potassium iodide and 38 g of iodine in 225 ml of water at room temperature. This mixture is further treated with a solution of 17.4 g of 1,4,5,6-tetrahydro-2-pyrimidinethiol in 350 ml of warm methanol, stirred for 2 hours and worked up in the manner described under Example 1 to yield 2-methyl-3-(1,4,5,6-tetrahydro-2-pyrimidinylthio)-indole hydriodide which melts at 242° after recrystallization from a mixture of methanol and ethyl acetate.

EXAMPLE 12

A solution of 8.6 g of 1-methylindole-2-carboxylic acid in 250 ml of warm methanol is added to a well-stirred solution of 25 g of potassium iodide and 12.2 g of iodine in 75 ml of water and treated with a solution of 5.8 g of 1,4,5,6-tetrahydro-2-pyrimidinethiol. The reaction is carried out and then worked up in the manner described under Example 1 to yield 1-methyl-3-(1,4,5,6-tetrahydro-2-pyrimidinylthio)-indole-2-carboxylic acid hydriodide which melts at 227° (with decomposition) after recrystallization from a mixture of methanol and ethyl acetate.

EXAMPLE 13

A solution of 13.1 g of 2-methylindole in 175 ml of warm methanol is added to a well-stirred solution of 50 g of potassium iodide and 25.4 g of iodine in 150 ml of water. This mixture is further treated with a hot solution of 10.2 g of 2-imidazolidinethione in 150 ml of warm methanol. The reaction is carried out and worked up in the manner described under Example 1 to yield 2-methyl-3-(2-imidazolin-2-ylthio)-indole hydriodide which melts at 227°–228° (with decomposition) after recrystallization from a mixture of methanol, ethyl acetate and ether.

EXAMPLE 14

A solution of 3.45 g of 5-methoxy-indole-2-carboxylic acid in 50 ml methanol is added to a solution of 4.57 g of iodine and 9 g of potassium iodide in 27 ml of water. This is treated with a solution of 2.34 g of 1-methyl-1,4,5,6-tetrahydro-2-pyrimidinethiol in 30 ml of water. The reaction is carried out and worked up as described under Example 1 to yield 5-methoxy-3-(1-methyl-1,4,5,6-tetrahydro-2-pyrimidinylthio)-indole-2-carboxylic acid hydriodide which melts at 256° (with decomposition) after recrystallization from a mixture of methanol and ethyl acetate.

EXAMPLE 15

A mixture of 5.85 g indole in 50 ml methanol and 5.8 g 1-methyl-2-imidazolidinethione in 100 ml methanol is treated with a solution of 12.7 g of iodine and 25 g potassium iodide in 100 ml water. The mixture is stirred for 2 hours at room temperature, the clear solution is concentrated in vacuo to one third of the original volume and cooled. The solid which separates is filtered off and recrystallized from a mixture of methanol and ethyl acetate to give 3-(1-methyl-2-imidazolin-2-ylthio)-indole hydriodide melting at 215°–216°.

EXAMPLE 16

A solution of 12.7 g of iodine and 25 g of potassium iodide in 100 ml of water is added dropwise to a mixture of 7.25 g of 1,2-dimethylindole in 60 ml methanol and 5.8 g of 1-methyl-2-imidazolidinethione in 100 ml methanol. The reaction mixture is stirred for 2 hours at room temperature. The crystalline precipitate formed was filtered and recrystallized from a mixture of methanol, ethyl acetate and ether to yield 1,2-dimethyl-3-(1-methyl-2-imidazolin-2-ylthio)-indole hydriodide which melts at 250°–251° (with decomposition).

EXAMPLE 17

A solution of 12.7 g of iodine and 20 g of potassium iodide in 100 ml water was added dropwise to a mixture of 7.25 g of 1,2-dimethylindole and 6.5 g of 1-methyl-1,4,5,6-tetrahydro-2-pyrimidinethiol in 120 ml methanol. The reaction mixture is stirred at room temperature for 2 hours. The crystalline precipitate formed was filtered and recrystallized from a mixture of methanol and ethyl acetate to yield 1,2-dimethyl-3-(1-methyl-1,4,5,6-tetrahydro-2-pyrimidinylthio)-indole hydriodide which melts at 239°–240° (with decomposition).

EXAMPLE 18

A solution of 12.7 g of iodine and 20 g of potassium iodide in 100 ml water is added dropwise to a mixture of 7.25 g of 1,2-dimethylindole in 30 ml of methanol and 5.8 g of 1,4,5,6-tetrahydro-2-pyrimidinethiol in 120 ml of warm methanol. The reaction mixture is stirred for 2 hours at room temperature. The crystalline precipitate formed was filtered and recrystallized from a mixture of methanol and ethyl acetate to yield 1,2-dimethyl-3-(1,4,5,6-tetrahydro-2-pyrimidinylthio)-indole hydriodide which melts at 246° (with decomposition).

EXAMPLE 19

A solution of 12.7 g of iodine and 20 g of potassium iodide in 100 ml of water is added dropwise to a solution of 7.25 g of indole in 30 ml methanol and 6.5 g of 4,5,6,7-tetrahydro-1H-1,3-diazepine-2-thiol in 100 ml of methanol. The reaction mixture is stirred for 2 hours at room temperature. The crystalline precipitate formed was filtered off and recrystallized from a mixture of methanol and ethyl acetate to afford 1,2-dimethyl-3-(4,5,6,7-tetrahydro-1H-1,3-diazepin-2-ylthio)-indole hydriodide of the formula

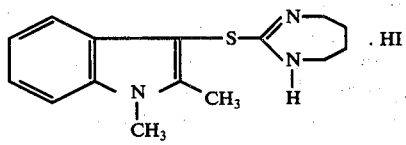

which melts at 245°–246° (with decomposition).

EXAMPLE 20

A solution of 12.7 g of iodine and 20 g of potassium iodide in 100 ml of water is added dropwise to a well-stirred mixture of 5.85 g of indole in 20 ml methanol and 6.5 g of 4,5,6,7-tetrahydro-1H-1,3-diazepine-2-thiol in 100 ml methanol. The reaction mixture is stirred at room temperature for 2 hours. The crystalline precipitate formed was filtered off and recrystallized from a mixture of methanol, ethyl acetate and ether to afford 3-(4,5,6,7-tetrahydro-1H-1,3-diazepin-2-ylthio)-indole hydriodide which melts at 236° (with decomposition).

EXAMPLE 21

To a stirred solution of 3.6 g 1,2-dimethylindole and 2.55 g 2-imidazolidinethione in 80 ml methanol is added a solution of 6.35 g iodine and 13 g potassium iodide in 50 ml water. After 1 hour at room temperature, the solution is concentrated in vacuo until crystals separate, then cooled and filtered. The precipitate is washed with water and ether and is recrystallized from alcohol to give 1,2-dimethyl-3-(2-imidazolin-2-ylthio)-indole hydriodide melting at 203°–205° (with decomposition).

EXAMPLE 22

To a stirred solution of 1.76 g indole and 1.5 g imidazole-2-thiol in 50 ml methanol is added a solution of 3.81 g iodine and 8 g potassium iodide in 30 ml water. After stirring for 3 hours at room temperature, the solution is concentrated in vacuo. An oil separates which crystallises upon addition of ether. The crystals are filtered off and washed with ethyl acetate; and finally recrystallized from a mixture of ethanol and ethyl acetate to give 3-(2-imidazol-2-ylthio)-indole hydriodide melting at 199°–201°.

EXAMPLE 23

A solution of 6.35 g of iodine and 11 g of potassium iodide in 50 ml of water is added dropwise to a mixture of 4.9 g of 5-bromoindole in 35 ml methanol and 3.25 g of 4,5,6,7-tetrahydro-1H-1,3-diazepine-2-thione in 50 ml of methanol. The reaction mixture is allowed to be stirred at room temperature for 2 hours. The crystalline precipitate formed is filtered off and recrystallized from a mixture of methanol and ethyl acetate to yield 5-bromo-3-(4,5,6,7-tetrahydro-1H-1,3-diazepin-2-ylthio)indole hydriodide which melts at 243°–246° (with decomposition).

We claim:

1. A pharmaceutical composition having vasoconstrictor and blood pressure lowering properties comprising a therapeutically effective amount of a compound of formula Ia

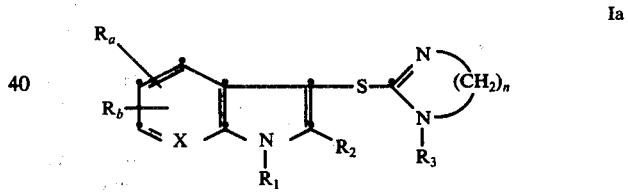

wherein X is nitrogen or the group CH, and each of $R_a$ and $R_b$ is hydrogen, lower alkyl, halogen or a lower alkoxy group, each of $R_1$ and $R_3$ independently is hydrogen or a lower alkyl group, $R_2$ is hydrogen, lower alkyl, a free carboxy group of a methoxy- or ethoxycarbonyl group and n is an integer denoting 2–4, or its tautomers or acid addition salts together with a pharmaceutically acceptable carrier.

2. A method for the treatment of a manual suffering from nasal congestion due to a cold which comprises administering to said mammal 0.1 to 50 mg. daily of a compound of the formula Ia as defined in claim 1.

3. A method of producing a blood pressure lowering effect in a mammal suffering from high blood pressure which comprises administering to said mammal 50 to 500 mg. daily of a compound of the formula Ia as defined in claim 1.